(12) United States Patent
McPeak

(10) Patent No.: US 10,478,213 B2
(45) Date of Patent: Nov. 19, 2019

(54) TISSUE-REMOVING CATHETER WITH ADJUSTABLE CROSS-SECTIONAL DIMENSION

(71) Applicant: Covidien LP, Mansfield, MA (US)

(72) Inventor: Thomas McPeak, Shakopee, MN (US)

(73) Assignee: Covidien LP, Mansfield, MA (US)

( * ) Notice: Subject to any disclaimer, the term of this patent is extended or adjusted under 35 U.S.C. 154(b) by 506 days.

(21) Appl. No.: 15/189,785

(22) Filed: Jun. 22, 2016

(65) Prior Publication Data

US 2016/0374715 A1   Dec. 29, 2016

Related U.S. Application Data

(60) Provisional application No. 62/184,489, filed on Jun. 25, 2015.

(51) Int. Cl.
| | | |
|---|---|---|
| *A61B 17/32* | (2006.01) | |
| *A61B 17/3207* | (2006.01) | |
| *A61B 17/22* | (2006.01) | |

(52) U.S. Cl.
CPC ............ *A61B 17/320725* (2013.01); *A61B 17/320758* (2013.01); *A61B 2017/22038* (2013.01); *A61B 2017/22061* (2013.01); *A61B 2017/320004* (2013.01)

(58) Field of Classification Search
CPC ............ A61B 17/320725; A61B 2017/22061
See application file for complete search history.

(56) References Cited

U.S. PATENT DOCUMENTS

| | | | |
|---|---|---|---|
| 4,966,604 A | 10/1990 | Reiss | |
| 5,030,201 A | 7/1991 | Palestrant | |
| 5,108,413 A | 4/1992 | Moyers | |
| 5,176,693 A | 1/1993 | Pannek, Jr. | |
| 5,279,565 A * | 1/1994 | Klein .................. | A61M 25/007 604/105 |
| 5,308,354 A | 5/1994 | Zacca et al. | |
| 5,376,100 A | 12/1994 | Lefebvre | |
| 5,490,859 A | 2/1996 | Mische et al. | |
| 5,653,690 A * | 8/1997 | Booth .................. | A61M 25/04 604/103.07 |
| 5,725,543 A * | 3/1998 | Redha .............. | A61B 17/32075 606/159 |
| 5,766,192 A | 6/1998 | Zacca | |
| 6,416,526 B1 | 7/2002 | Wyzgala et al. | |
| 6,497,711 B1 | 12/2002 | Plaia et al. | |
| 6,800,083 B2 | 10/2004 | Hiblar et al. | |

(Continued)

FOREIGN PATENT DOCUMENTS

| | | |
|---|---|---|
| EP | 0442137 A1 | 8/1991 |
| EP | 0 533 321 A2 | 3/1993 |
| WO | 2005030061 A1 | 4/2005 |

OTHER PUBLICATIONS

International Search Report and Written Opinion for PCT/US2016/039072, dated Sep. 15, 2016, 14 pages.

*Primary Examiner* — Alexander J Orkin

(57) ABSTRACT

A tissue-removing catheter includes a drive shaft and a tissue-removing head. The tissue-removing head is at the distal end of the drive shaft and is configured to rotate about a longitudinal axis of the drive shaft. The tissue-removing head is selectively adjustable from an initial cross-sectional dimension to an expanded cross-sectional dimension larger than the initial cross-sectional dimension.

13 Claims, 4 Drawing Sheets

(56) References Cited

U.S. PATENT DOCUMENTS

| | | |
|---|---|---|
| 7,252,674 B2 | 8/2007 | Wyzgala et al. |
| 8,109,957 B2* | 2/2012 | Stad ............... A61B 17/320725 |
| | | 606/170 |
| 2003/0135218 A1* | 7/2003 | Eckman ............. A61B 17/1671 |
| | | 606/79 |
| 2006/0178685 A1 | 8/2006 | Melsheimer |
| 2007/0270863 A1* | 11/2007 | Melkent ............. A61B 17/1659 |
| | | 606/79 |
| 2009/0306690 A1 | 12/2009 | Rivers et al. |
| 2018/0263654 A1* | 9/2018 | Steele ............ A61B 17/320758 |

* cited by examiner

TISSUE-REMOVING CATHETER WITH ADJUSTABLE CROSS-SECTIONAL DIMENSION

CROSS-REFERENCE TO RELATED APPLICATIONS

The present application claims the benefit of U.S. Provisional Application Ser. No. 62/184,489, filed Jun. 25, 2015, the entirety of which in incorporated by reference.

FIELD OF THE DISCLOSURE

The present disclosure generally relates to a tissue-removing catheter with a rotatable tissue-removing head having an adjustable cross-sectional dimension.

BACKGROUND

The patency of a body lumen may be affected by the build-up of tissue or other material in the body lumen. A variety of methods for cutting or dislodging occlusive material and removing such material from a body lumen, such as a blood vessel, have been proposed. For example, tissue-removing catheters may be used to restore the patency of a body lumen. These catheters are intended to cut or excise material from the body lumen and may employ a rotatable tissue-removing element which can be advanced into or past the occlusive material in order to cut and separate such material from the body lumen.

Although these catheters have proven very successful in restoring the patency of body lumens, problems may arise when the tissue-removing element has a smaller diameter than the occlusive tissue. If the tissue-removing element does not maintain contact with the occlusion or lumen wall, the efficacy of the tissue-removing element is reduced.

SUMMARY

In one aspect, a tissue-removing catheter includes a tissue-removing head that is selectively adjustable from an initial cross-sectional dimension to an expanded cross-sectional dimension larger than the initial cross-sectional dimension.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
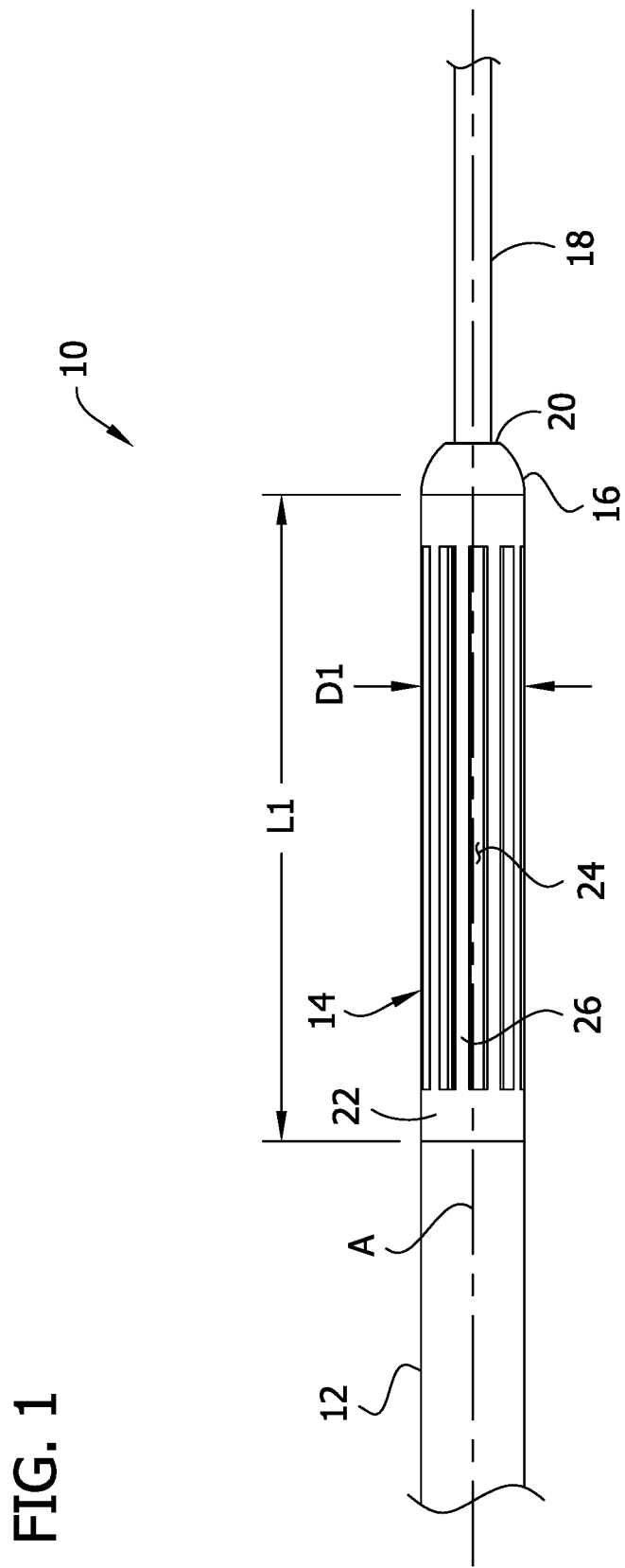
FIG. 1 is an enlarged, partial perspective of an embodiment of a tissue-removing catheter, a tissue-removing head of the device being in an initial configuration.
Figure 2:
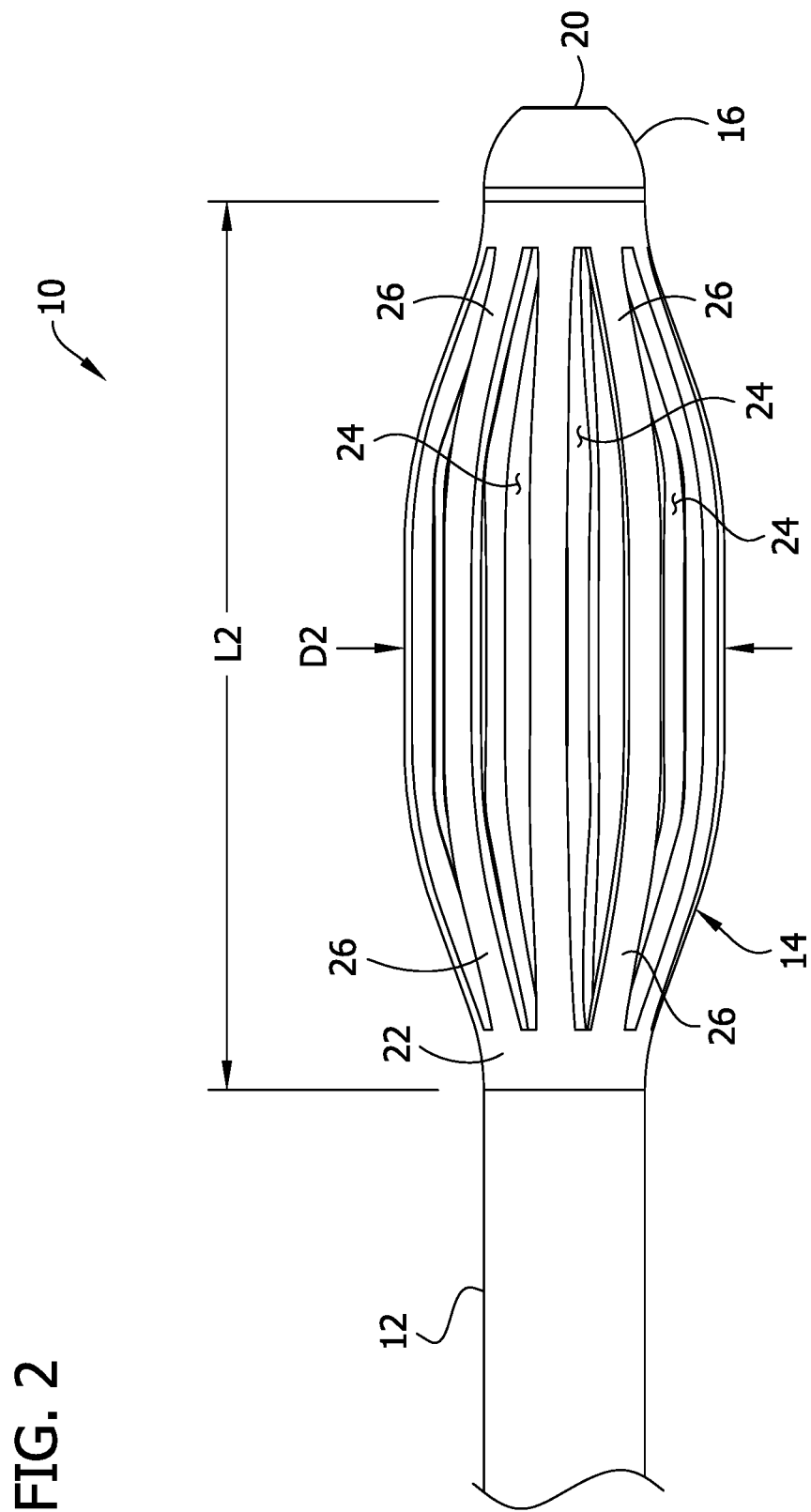
FIG. 2 is similar to FIG. 1, illustrating the tissue-removing head in an expanded configuration.
Figure 3:
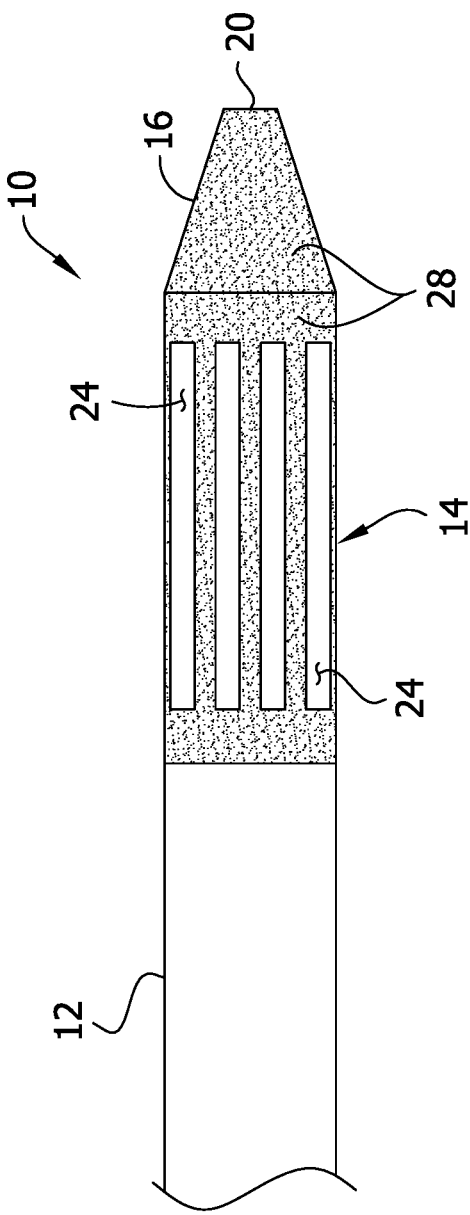
FIG. 3 is schematic of the tissue-removing catheter with the tissue-removing head in the initial configuration, illustrating an abrasive exterior surface of the tissue-removing catheter.

Referring to FIGS. 1-3, an embodiment of a tissue-removing catheter for removing tissue from a body lumen is generally indicated at reference numeral 10. The illustrated tissue-removing catheter 10 is particularly suitable for removing an atheroma (e.g., plaque) from a blood vessel, although the catheter may be used to remove other occlusions from other body lumens.

The tissue-removing catheter 10 comprises a drive shaft 12, a tissue-removing head, generally indicated at 14, disposed at a distal end of the drive shaft, and a distal cap 16 disposed at a distal end of the tissue-removing head. The drive shaft 12 is operable to rotate the tissue-removing head 14 and the distal cap 16 about an axis A to remove tissue from a lesion or obstruction in a body lumen. The drive shaft 12, head 14, and cap 16 define a guide wire lumen 19 to receive a guide wire 18. The cap 16 includes a distal opening 20 through which the guide wire 18 extends. The tissue-removing catheter 10 is configured for use as an over-wire device (i.e., over the guide wire 18). However, other configurations are within the scope of the present invention, and it is understood that the guide wire 18 may be omitted within the scope of the present invention. As shown in FIGS. 1-3 and other drawings, the illustrated cap 16 has a generally conical or dome-shape that tapers distally and is suitable for boring through tissue (e.g., plaque) occluding a body lumen. A specialty wire may be used in conjunction with the tissue-removing catheter 10 to facilitate coring through total or near total occlusions.

The tissue-removing head 14 includes a generally tubular body 22 having circumferentially spaced longitudinal slots 24 separating fingers 26. The longitudinal slots 24 permit the head 14 to expand circumferentially, as described below. The head 14 is made of Nitinol, spring steel, or any other suitable material. A proximal end of the head 14 is fixedly attached to the drive shaft 12 such that the drive shaft imparts rotation of the head. The drive shaft 12 may be formed separately from the head 14, or may be integrally formed therewith. A proximal end of the cap 16 is fixedly attached to a distal end of the head 14 opposite the drive shaft 12. The cap 16 is attached to the head 14 such that the cap moves (e.g., rotates) with the head. The cap 16 may be formed separately from the head 14, or may be integrally formed therewith. At least a portion of the cap 16 and/or at least a portion of the head 14 has an abrasive exterior surface for abrading a lesion in a body lumen. For example, an abrasive material or grit 28 may be applied to at least a portion of the exterior surface of the cap 16 or the head 14, or the exterior surface may otherwise be formed to be abrasive. In one embodiment, a portion of the cap 16 and/or a portion of the head 14 is coated with an abrasive coating or grit 28. In the illustrated embodiment, the exterior surfaces of both the cap 16 and the head 14 are coated with grit 28. The grit 28 abrades and removes tissue from a body lumen as the catheter rotates about the axis A. The grit can be diamond grit or other suitable material for use on a rotary head for removing tissue.

Figure 4:
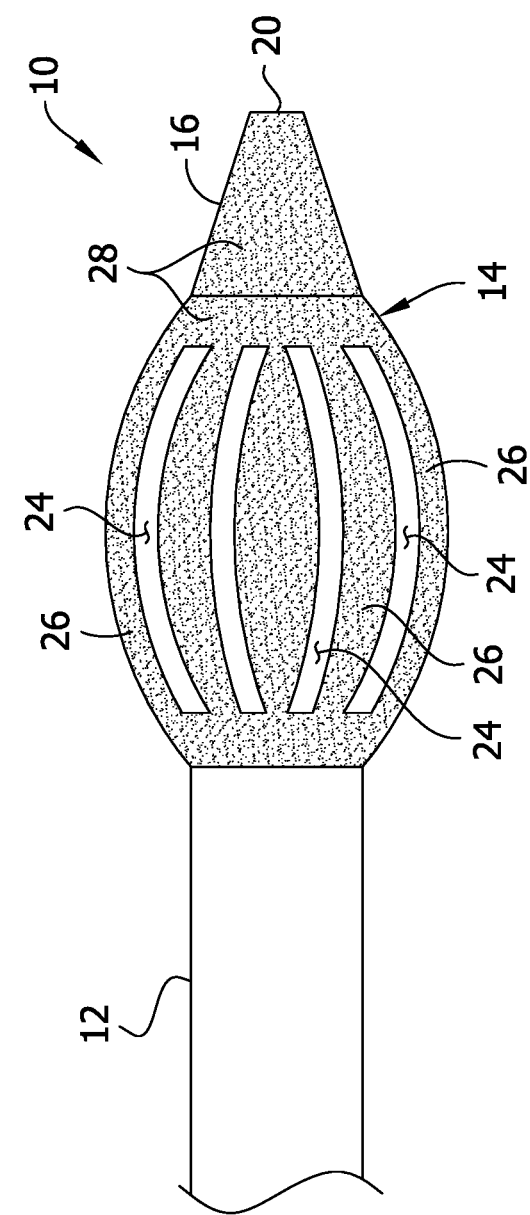
FIG. 4 is similar to FIG. 3, but with the tissue-removing head in the expanded configuration.

The tissue-removing head 14 has an initial or minimum cross-sectional dimension D1 (see FIG. 1) and a first longitudinal length L1. The head 14 is expandable circumferentially to increase the cross-sectional dimension to an expanded or maximum cross-sectional dimension D2 (FIGS. 2 and 4), which is larger than the initial cross-sectional dimension D1. As illustrated, the initial cross-sectional dimension D1 is about the same as a cross-sectional dimension of the drive shaft 12 and the expanded cross-sectional dimension D2 is larger than the cross-sectional dimension of the drive shaft, although other configurations are within the scope of the present invention. In the expanded configuration, the fingers 26 of the head 14 flex or bend outward to increase the cross-sectional dimension of the head, which, in turn, shortens the tissue-removing head to a second longitudinal length L2. Thus, as the cross-sectional dimension of the head 14 increases, the longitudinal length of the head decreases. The head 14 can be expanded and contracted to have any cross-sectional dimension in the range between the initial cross-sectional dimension D1 and a maximum expanded cross-sectional dimension D2.

Figure 5:
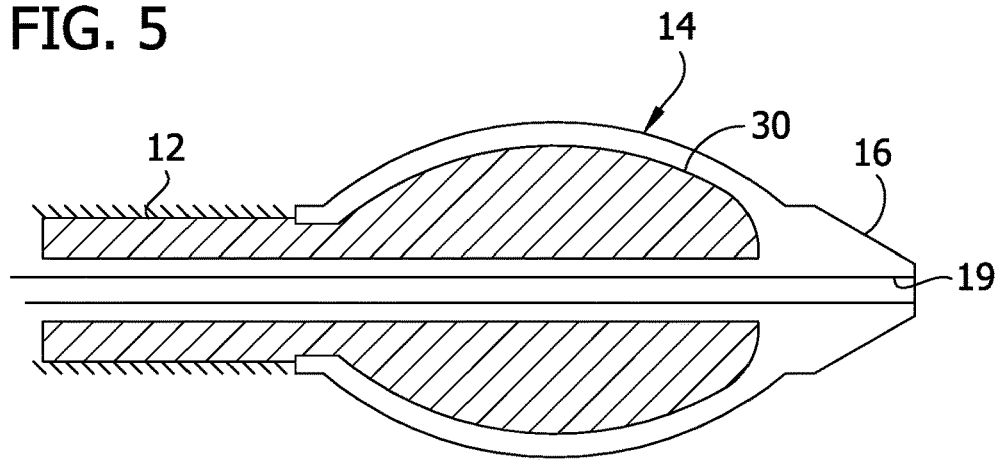
FIG. 5 is a schematic of one embodiment of an expanding mechanism, illustrating a balloon inflated to expand the tissue-removing head.

The illustrated tissue-removing catheter 10 includes an expansion mechanism for use in circumferentially expanding the head 14. In the embodiment illustrated in FIG. 5, the device 10 includes a balloon 30 positioned in the interior of the head 14. The balloon 30 is inflated and deflated to control the cross-sectional dimension of the head 14. The balloon 30 rotates with the drive shaft 12, the head 14, and the cap 16. The balloon 30 is disposed on a balloon shaft having a lumen for use in inflating the balloon. The balloon 30 is inflated or deflated by a rotating pressure port (not shown) on a proximal end of the tissue-removing catheter. As the balloon 30 is inflated, it pushes the fingers 26 of the head 14 radially outward to expand the circumference of the head. When the balloon 30 is deflated, the head 14 returns to its initial cross-sectional dimension. The head 14 is adjustable to different cross-sectional dimensions based on the amount the balloon 30 is inflated.

Figure 6:
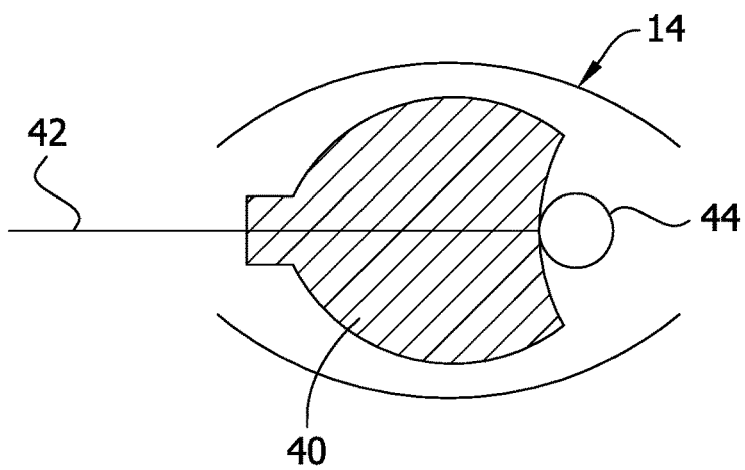
FIG. 6 is a schematic of another embodiment of an expanding mechanism, illustrating a wire, ball, and elastomer used to expand the tissue-removing head.

In another embodiment, illustrated in FIG. 6, an elastomer 40 is positioned in the interior of the head 14. A movable cone or ball 44 (broadly, an actuator) is attached to a distal end of a wire 42 which extends proximally through the drive shaft 12. A user pushes or pulls the wire 42 to move the ball 44 against the elastomer 40, thereby causing the elastomer to compress and bulge radially outward. As the elastomer 40 bulges radially outward, it pushes the fingers 26 of the head 14 radially outward to expand the circumference of the head. Alternatively, a threaded rod or other device used to impart movement of the ball relative to the elastomer can be used in place of the wire 42.

Figure 7:
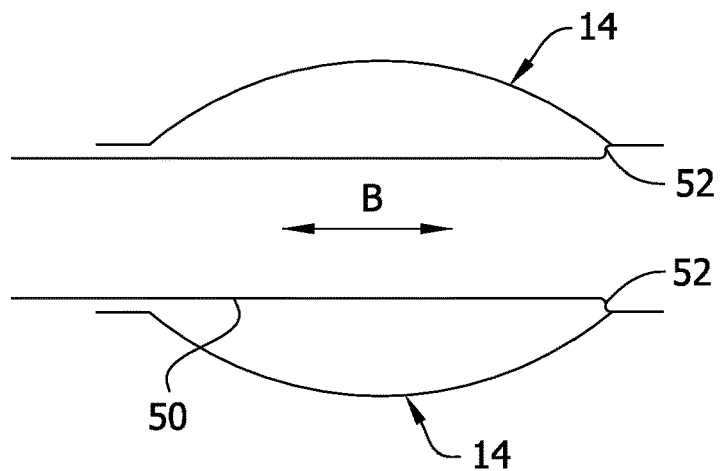
FIG. 7 is a schematic of another embodiment of an expanding mechanism, illustrating a tube fixed at one end for use in expanding the tissue-removing head.

In yet another embodiment, illustrated in FIG. 7, an inner tube 50 is fixedly attached at one end to the head 14 at attachment points 52. The inner tube 50 is movable relative to the drive shaft 12. As the inner tube 50 is moved, the distal end of the head 14 moves with the inner tube because of the attachment of the inner tube to the head. Longitudinal movement in the direction of arrows B of the inner tube 50 causes the fingers 26 of the head 14 to bow outward or inward to reduce or increase the length of the head, thereby increasing or decreasing the cross-sectional dimension of the head. Other suitable mechanisms for expanding and contracting the cross-sectional dimension of the head 14 are within the scope of the present invention.

Although not illustrated, a control handle or other control device operatively connects to the tissue-removing catheter 10. The control handle includes a housing and at least one actuator in the housing for driving rotation of the driveshaft. In one example, the control handle may include a rotary actuator for rotating the driveshaft about the axis A. The control handle can also include an actuator for adjusting the cross-sectional dimension of the head 14 (e.g., to adjust inflation of balloon 30, move wire 42, move tube 50, or other suitable mechanism for adjusting the cross-sectional dimension of the head).

In one embodiment of a tissue-removing operation, the tissue-removing catheter 10 is advanced in a body lumen over the guide wire 18 to a target site (e.g., a lesion in the body lumen). At the target site, the tissue-removing catheter 10 can be activated using the control handle, such as by activating a control lever, button, or other device to activate the at least one actuator. Upon activating the tissue-removing catheter 10, the drive shaft 12 rotates about the axis A, causing rotation of the head 14 and the cap 16. The head 14 and/or the cap 16 abrades the lesion, thereby removing tissue. The cross-sectional dimension of the head 14 can be expanded (e.g., by using the control handle to inflate the balloon 30) to enlarge an existing lumen by abrading and removing additional tissue from the lesion.

The tissue-removing catheter 10 may also be used without a guide wire. In one embodiment, the cap 16 is used to bore through a near total or total occlusion. The tissue-removing catheter 10 may also be used without imparting rotation of the tissue-removing head. In one embodiment, the tissue-removing head 14 is used to center the tissue-removing catheter 10 in the true lumen (i.e., in the space remaining between occlusions in the body lumen). The tissue-removing head 14 can be expanded circumferentially to contact the outer limits of the true lumen, thereby centering the tissue-removing catheter 10 in the true lumen. With the catheter 10 centered in the true lumen, a wire (e.g., guide wire 18) can be advanced beyond the cap 16 to bore through tissue occluding the body lumen. In one embodiment, the tissue-removing head 14 can be advanced in the initial configuration to a target site, and then expanded circumferentially at the target site to engage the occlusion to cut or tear the occlusion without rotating the tissue-removing head. In one embodiment, the tissue-removing head 14 can be advanced beyond a target site, then expanded circumferentially and pulled back over the target site to remove tissue. An aspiration catheter (not shown) can be positioned near that tissue-removing head to collect debris removed by the tissue-removing head.

The tissue-removing catheter 10 facilitates creation of a larger lumen diameter. The head 14 can increase in cross-sectional dimension to continue to enlarge an existing lumen (e.g., by using multiple passes over the same lesion), treat multiple vessels in the same patient, or treat vessels that have slight to moderate aneurysmal pockets. Because the head 14 can decrease in cross-sectional dimension after it has been expanded, it may allow a practitioner to retrieve a stuck head or treat disease that is distal to a treatment barrier such as a stent. The variable cross-sectional dimension head 14 reduces the need for using different size heads to treat multiple diameters or vessels, resulting in decreased costs. It also does not rely on centrifugal force (and thus, require a high-speed, well controlled motor) to maintain contact between the head 14 and the lesion, but rather expands the head to contact the lesion which may result in further cost savings.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical device comprising:
   a tissue-removing catheter comprising:
   a drive shaft having opposite proximal and distal ends and configured for rotation about a longitudinal axis;
   a tissue-removing head at the distal end of the drive shaft, wherein the tissue-removing head is configured to rotate about the longitudinal axis, and wherein the tissue-removing head is selectively adjustable from an initial cross-sectional dimension to an expanded cross-sectional dimension larger than the initial cross-sectional dimension; and
   an expansion mechanism configured to selectively adjust the tissue-removing head from the initial cross-sectional dimension to the expanded cross-sectional dimension, wherein the expansion mechanism includes an elastically deformable member disposed inside the tissue-removing head, wherein the elastically deformable member is selectively elastically compressible in a longitudinal direction to increase a cross-sectional dimension of the elastically deformable member from an initial cross-sectional dimension to an expanded cross-sectional dimension greater than the initial cross-sectional dimension when the elastically deformable member is longitudinally compressed to selectively adjust the tissue-removing head from the initial cross-sectional dimension to the expanded cross-sectional dimension;
   wherein the expansion mechanism includes an actuator and the tissue-removing catheter houses the actuator, the actuator being selectively movable axially within the tissue-removing head to elastically compress the elastically deformable member.

2. The medical device set forth in claim 1, wherein the expansion mechanism includes a wire extending along the drive shaft, the wire being selectively moveable axially relative to the drive shaft and the tissue-removing head, wherein the actuator is secured to the distal end of the wire.

3. The medical device set forth in claim 2, wherein the wire is disposed in an axial lumen extending along the drive shaft.

4. The medical device set forth in claim 2, wherein the wire is selectively movable proximally relative to the drive shaft to move the actuator proximally relative to the tissue-removing head to elastically compress the elastically deformable member.

5. The medical device set forth in claim 2, wherein the wire is selectively movable distally relative to the drive shaft to move the actuator distally relative to the tissue-removing head to elastically compress the elastically deformable member.

6. The medical device set forth in claim 5, wherein the actuator comprises a cone or ball member.

7. The medical device set forth in claim 1, wherein the tissue-removing head comprises an abrasive exterior surface configured to abrade tissue as the tissue-removing head rotates about its longitudinal axis.

8. The medical device set forth in claim 7, wherein the tissue-removing head comprises a generally tubular body including longitudinal fingers spaced apart from one another circumferentially about the longitudinal axis of the tissue-removing head to define a plurality of circumferentially spaced longitudinal slots.

9. A method of debulking a body lumen, the method comprising:
   delivering a distal end of a tissue-removing catheter to a target site within the body lumen, the tissue-removing catheter including
      a drive shaft having opposite proximal and distal ends and configured for rotation about a longitudinal axis, and
      a tissue-removing head at the distal end of the drive shaft, wherein the tissue-removing head is configured to rotate about the longitudinal axis, and wherein the tissue-removing head is selectively adjustable from an initial cross-sectional dimension to an expanded cross-sectional dimension larger than the initial cross-sectional dimension;
   adjusting the tissue-removing head from the initial cross-sectional dimension to the expanded cross-sectional dimension, wherein said adjusting the tissue-removing head comprises elastically compressing an elastically deformable member disposed inside the tissue-removing head in a longitudinal direction to increase a cross-sectional dimension of the elastically deformable member from an initial cross-sectional dimension to an expanded cross-sectional dimension greater than the initial cross-sectional dimension to selectively adjust the tissue-removing head from the initial cross-sectional dimension to the expanded cross-sectional dimension;
   rotating the drive shaft about its longitudinal axis to impart rotation of the tissue-removing head, wherein the rotating tissue-removing head removes tissue from a wall of the body lumen at the target site.

10. The method of debulking a body lumen set forth in claim 9, wherein the tissue-removing head includes an abrasive exterior surface, wherein the rotating tissue-removing head abrades tissue from the wall of the body lumen.

11. The method of debulking a body lumen set forth in claim 9, wherein said adjusting the tissue-removing head comprises axially moving an actuator within the tissue-removing head to elastically compress the elastically deformable member.

12. The method of debulking a body lumen set forth in claim 11, wherein said axially moving an actuator comprises moving the actuator proximally.

13. The method of debulking a body lumen set forth in claim 11, wherein said axially moving an actuator comprises moving the actuator distally.

* * * * *